United States Patent [19]

Wiener

[11] 4,420,851
[45] Dec. 20, 1983

[54] MECHANIZED TOOTH BRUSH HAVING MOVEMENT IN TWO PLANES

[76] Inventor: Stanley M. Wiener, 1857 Floyd St., Sarasota, Fla. 33579

[21] Appl. No.: 328,373

[22] Filed: Dec. 7, 1981

[51] Int. Cl.³ .............................................. A46B 13/02
[52] U.S. Cl. ..................................... 15/22 R; 15/28; 74/22 R; 192/0.02 R
[58] Field of Search .................. 15/22 R, 22 A, 22 C, 15/23, 24, 28, 29, 97 R; 74/22 R; 192/0.02 R, 21.5, 84 R, 84 E, 84 PM; 51/170 R

[56] References Cited

U.S. PATENT DOCUMENTS 3,270,360 9/1966 Kropp ................................. 15/22 R
3,822,432 7/1974 Skinner ................................ 15/28

FOREIGN PATENT DOCUMENTS 2400787 7/1975 Fed. Rep. of Germany ..... 15/22 R
1267147 6/1961 France .................................... 15/28
546038 6/1956 Italy ....................................... 15/28

Primary Examiner—Edward L. Roberts
Attorney, Agent, or Firm—George B. Oujevolk

[57] ABSTRACT

An elongated tooth brush handle houses a motor at the bottom of the handle. The motor output shaft is surrounded by an inner magnet which in turn is coupled to an outer magnet. When opposite poles face each other the inner magnet will turn the outer magnet. The outer magnet turns on a bearing which will give it longitudinal motion. The outer magnet is coupled to flexible shaft which passes out of the head of the handle to an output coupling through a slit in the handle head. A small rotary brush can be affixed to the output coupling.

1 Claim, 3 Drawing Figures

U.S. Patent   Dec. 20, 1983   4,420,851
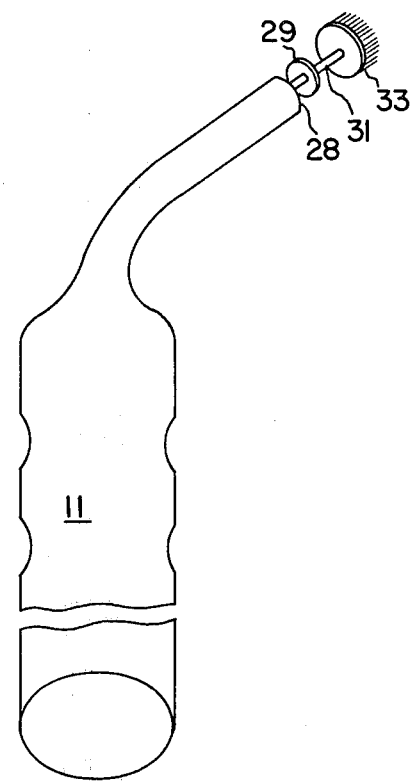
FIG. I
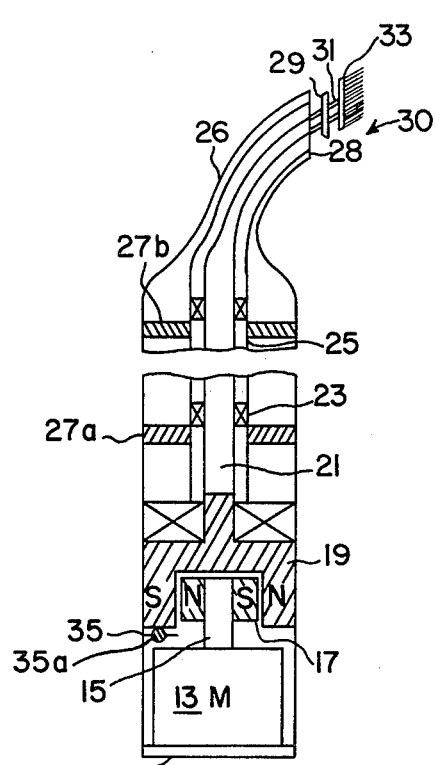
FIG. 2
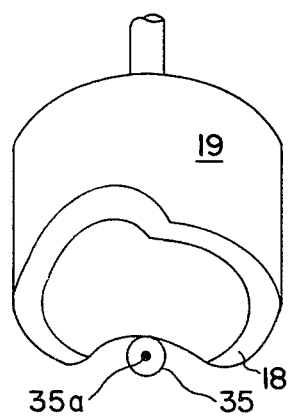
FIG. 3

MECHANIZED TOOTH BRUSH HAVING MOVEMENT IN TWO PLANES

BACKGROUND OF THE INVENTION

The present invention relates to mechanized tooth brushes and more particularly to a mechanized tooth brush arrangement which will clean between teath and with a weak link to avoid damage to the teeth.

BRIEF DESCRIPTION OF THE PRIOR ART

Heretofore, tooth brushes, especially mechanized tooth brushes would either move in a longitudinal motion or a rotary motion. The longitudinal motion was used mostly for home tooth brushes while the rotary motion was used by dentists. Neither of these tooth brushes go between teeth and the usual dentist recommendation is to use dental floss.

OBJECT OF THE INVENTION

The present invention is directed to a mechanical tooth brush designed to provide an arrangement which will not only move in one plane, but in several planes so as to force the brush hairs between teeth but will not damage the teeth because of a weak link in the clutch mechanism which will not transmit power to the brush when it encounters too much resistance.

SUMMARY OF THE INVENTION

Generally speaking the present invention contemplates an elongated tooth brush handle which houses a motor at the bottom of the handle. The motor output shaft is surrounded by an inner magnet which in turn is opposite an outer magnet. When opposite poles face each other the inner magnet will turn the outer magnet. The outer magnet turns on a bearing which will give it longitudinal motion. The outer magnet is coupled to a flexible shaft which passes out of the head of the handle through a slit in the handle head. A small rotary brush can be affixed to the output coupling at the outer end of the flexible shaft.

The invention as well as other objects and advantages will be more apparent from the following detailed description and the accompanying drawings, in which:

BRIEF DESCRIPTION OF THE DRAWINGS

FIG. 1 is a perspective view of the tooth brush cylindrical holder holding a brush rotating at an angle to the longitudinal plane of the cylindrical holder;

FIG. 2 presents a cross-sectional explanation of the components held in the holder shown in FIG. 1; and, FIG. 3 illustrates the component providing longitudinal as well as rotary motion to the brush in perspective.

DETAILED DESCRIPTION

Shown in the drawing is an elongated cylindrical, curved neck brush holder 11 acting as the housing. At the bottom end 12 of this cylindrical holder 11 is a motor 13 which has an output shaft 15. Around the output shaft 15 is a cylindrical inner magnet 17. This magnet 17 has two lateral poles. Disposed over inner magnet 17 is a cup-shaped outer magnet 19 which likewise has two lateral poles so that when placed over the inner magnet 15 a magnetic clutch is formed. The rim of the cup-shaped magnet 19 does not lie in one plane but as shown in FIG. 3, rim 18 is somewhat sinusoidal in shape so that as the cup-shaped outer magnet 19 rotates, the magnet can be made to move longitudinally.

Affixed to the cup-shaped outer magnet 19 is a flexible shaft 21 which is held for rotation by bearings 23 and enters a guide tube 25 held by brackets 27a, 27b. Guide tube 25 has a curved portion and extends to an outlet orifice 28 where the flexible shaft 21 exits the head 30 of the cylindrical housing 11, here the flexible shaft 21 enters an output coupling 29.

To exit the head 30 and have movement in the longitudinal plane of the cylindrical holder 11, orifice 28 is a slit or oval-shaped aperture. The output coupling 29 has a receiving aperture (not shown) to receive a brush shaft 31 of the brush 33. Brush 33 is removable and can come in various designs. If necessary, or desired, the disc-shaped base of brush 33 can be mounted on its shaft 31 so that the center is offset to enhance the non-linear movement of the brush which will enable the brush hairs to enter between the teeth.

By using a magnetic clutch, a weak link is provided so that if the brush encounters too much resistance it will not break or chip the teeth.

The rim 18 of the cup-shaped magnet rides over a bearing 35. As can be seen in FIG. 2, bearing 35 has an axle pin 35a, which serves to hold the bearing to the cylindrical holder 11. The reciprocating movement of the cup-shaped magnet 19 is provided by the magnetic attractive force between the inner magnet 17 and the cup-shaped magnet 19. This force tends to continuously force the magnets to the center of the magnetic field. The motor rotates the inner magnet 17, which compels the cup-shaped magnet 19 to follow it in rotation. As the cup-shaped magnet 19 rotates, its face or lower rim 18 having a sinusoidal shaped cam surface bears continuously on bearing 35 which is held to the cylindrical holder 11 by the axle pin 35a.

Since, as shown in FIG. 2, the inner magnet 17 is positioned on the inside the cup-shaped magnet 19 and, as hereinbefore stated both magnets have lateral poles, there is always a longitudinal magnetic attraction between these two magnets which compels the cup-shaped magnet towards bearing 35. Bearing 35 is a simple, low friction ball with an axle pin 35a. Brackets 27a and 27b as well as bearing 23 are made of low friction material such as teflon, duralon, oilite, etc. which permit longitudinal as well as rotational movement. As shown in FIG. 2, the bearing 23 is connected to bracket 27a.

Since the rim 18 has a sinusoidal shape, the cup-shaped outer magnet 19 will move longitudinally in the cylindrical brush holder 11.

The flexible shaft used herein is described in Stow FLEXIBLE SHAFT ENGINEERING HANDBOOK Stow Mfg. Co. Binghamton, N.Y. 7th Ed. 1973 and is commercially available.

What is claimed is:

1. A mechanical tooth brush having rotary and longitudinal motion comprising:
   an elongated cylindrical housing;
   said housing contains a motor located at a first end of said housing;
   said housing contains an orifice at a second end opposite to said first end at which said motor is located within said housing;
   an output shaft is connected to said motor;
   an inner magnet is connected to said output shaft; said inner magnet is perpendicular to said output shaft;

a flexible shaft extends through the interior of said housing and passes outside said housing through said orifice;

a guide tube guides said flexible shaft through said interior of said housing until reaching said orifice;

said flexible shaft adapted for slidable longitudinal motion within said guide tube;

said flexible shaft exits said housing and is connected to an output coupling at a first end of said flexible shaft outside of said interior of said housing;

a cup-shaped magnet is connected to a second end of said flexible shaft within housing, opposite to said first end of said flexible shaft;

said cup-shaped magnet forms a first edge shaped in a circular, sinusoidal wave;

a bearing rotatable on a bearing shaft;

said first edge of said cup-shaped magnet bears continuously on said bearing, to provide said flexible shaft with longitudinal motion as said flexible shaft rotates; and said cup-shaped magnet is disposed over and around said inner magnet.

* * * * *